United States Patent
Sato et al.

(10) Patent No.: US 6,900,330 B1
(45) Date of Patent: May 31, 2005

(54) PROCESS FOR PRODUCING 2,3-PYRIDINEDICARBOXYLIC ACID

(75) Inventors: Toshio Sato, Kashima (JP); Takeshi Namekata, Kashima (JP)

(73) Assignee: Hebei Sinochem Fuheng Co., Ltd., Hebei (CN)

( * ) Notice: Subject to any disclaimer, the term of this patent is extended or adjusted under 35 U.S.C. 154(b) by 0 days.

(21) Appl. No.: 10/657,732

(22) Filed: Sep. 8, 2003

(30) Foreign Application Priority Data

Dec. 10, 2002 (JP) ........................................ 2002-358020

(51) Int. Cl.$^7$ .......................................... C07D 213/807
(52) U.S. Cl. ...................................... 546/320; 546/319
(58) Field of Search ................................. 546/319, 320

(56) References Cited

U.S. PATENT DOCUMENTS

| | | | | |
|---|---|---|---|---|
| 4,537,971 A | * | 8/1985 | Rebhahn et al. | ............ 546/320 |
| 4,754,039 A | * | 6/1988 | Michalowicz | ............... 546/320 |

FOREIGN PATENT DOCUMENTS

| | | |
|---|---|---|
| JP | 49-55673 | 2/1974 |
| JP | 60-54305 | 3/1981 |
| JP | 58-105964 | 6/1983 |
| JP | 61-212563 | 9/1986 |
| JP | 62-18551 | 3/1987 |
| JP | 62-209063 | 6/1988 |
| JP | 02-083370 | 3/1990 |
| JP | 03-271275 | 3/1991 |
| JP | 03-101661 | 4/1991 |
| JP | 03-157371 | 7/1991 |
| JP | 03-287576 | 12/1991 |

OTHER PUBLICATIONS

C. O'Murchu, Ozonolysis of Quinolines: A Versatile Synthesis of Polyfunctional Pyridines, Synthesis, 11, 1989, pp. 880–882.
Walter Stix Und S.A. Bulgatsch: Eine Neue Darstellungsart Der Chinolinsäure, Chem. Ber. 65 11–13 (1932).
W. Koenigs: Oxydation Des Cinchoninchinolins Mittelst Kaliumpermanganat, Chem. Ber. 12, 983–984 (1879).
C. O'Murchu, Ozonolysis of Quinolines: A Versatile Synthesis of Polyfunctional Pyridines, Synthesis, 11, 1989, pp. 880–882.

* cited by examiner

*Primary Examiner*—Patricia L. Morris
(74) *Attorney, Agent, or Firm*—The Webb Law Firm

(57) ABSTRACT

Highly pure 2,3-pyridinedicarboxylic acid is produced by a process suitable for application in commercial production with a high yield and with recirculation of waste liquor. The process comprises the steps of: (a) oxidizing quinoline or 8-hydroxyquinoline in a solvent in the presence of copper (II) ions to precipitate copper (II) salt of 2,3-pyridinedicarboxylic acid and then separate the precipitates, (b) reacting the separated copper (II) salt with an alkali in a solvent to obtain a solution of an alkali metal salt of 2,3-pyridinedicarboxylic acid, and (c) reacting the solution of the alkali metal salt with a mineral acid to precipitate 2,3-pyridinedicarboxylic acid and then separate the precipitates, and is characterized in that (A) part or all of the solution obtained after the precipitated 2,3-pyridinedicarboxylic acid is separated in step (c) is used as at least part of the solvent in step (a) or (b), or (B) copper or a copper compound is added to the solution obtained after the precipitated 2,3-pyridine-dicarboxylic acid is separated in step (c) to recover the 2,3-pyridinedicarboxylic acid remaining in the solution as its copper (II) salt.

5 Claims, No Drawings

PROCESS FOR PRODUCING 2,3-PYRIDINEDICARBOXYLIC ACID

TECHNICAL FIELD

The present invention relates to a process for producing 2,3-pyridine-dicarboxylic acid starting from quinoline or 8-hydroxyquinoline via the copper (II) salt of this acid. The process according to the present invention is suitable for commercial production of 2,3-pyridinedicarboxylic acid since it makes it possible to decrease the amount of waste liquor discharged from the process and at the same time to obtain a high-purity product with a significantly increased yield.

BACKGROUND ART 2,3-Pyridinedicarboxylic acid, which is also called quinolinic acid, has a wide variety of uses as intermediates in the production of medicinal or agricultural chemicals, dyes, pigments, and the like.

A number of methods with respect to the preparation of 2,3-pyridine-dicarboxylic acid have been investigated. There have been proposed, for example, a method in which quinoline is oxidized in sulfuric acid with hydrogen peroxide or sodium chlorate in the presence of a ruthenium compound as a catalyst (JP-A 03-271275), a method in which quinoline or 8-hydroxyquinoline is oxidized with hypochlorite ions in the presence of a ruthenium compound as a catalyst (JP-A 61-212563, JP-A 02-83370, and JP-A 03-101661), a method in which quinoline is oxidized with chlorite ions in the presence of a ruthenium compound as a catalyst (JP-A 03-157371), a method in which quinoline is oxidized with oxygen in the presence of a large amount of cobalt ions (JP-A 49-55673), and a method in which 8-hydroxyquinoline is oxidized with chlorate ions in the presence of vanadium ions (JP-A 58-105964).

A method in which quinoline is oxidized with sodium chlorate under acidic conditions in the presence of an equimolar amount of a copper (II) salt is described in JP-A 62-209063. Another method in which quinoline is oxidized in two steps using a chlorate salt in the final oxidation step is described in JP-B 62-18551. Other known methods include a method in which quinoline is oxidized with hydrogen peroxide in the presence of copper (II) ions [Chem. Ber. 65, 11 (1932)], a method in which 8-hydroxyquinoline is oxidized with nitric acid [Chem. Ber. 12, 983 (1879)], and a method in which quinoline is oxidized with ozone [Synthesis, 11, 880 (1989)].

As an improvement on the method described in Chem. Ber. 65, 11 (1932) in which quinoline is oxidized with hydrogen peroxide in the presence of copper (II) ions, it is described in JP-B 60-54305 that an increased yield is attained by performing the reaction under acidic conditions with sulfuric acid, collecting the resulting quinolinic acid copper (II) salt by filtration, and recirculating the filtrate for repeated use as a reaction medium for the oxidation reaction.

As described above, a great number of methods have been proposed with respect to the production of 2,3-pyridinedicarboxylic acid by oxidation of quinoline or its derivative. Seen the other way around, this indicates that there is no method which has been established for commercial production of 2,3-pyridinedicarboxylic acid.

At present, 2,3-pyridinedicarboxylic acid is commercially produced by a method in which quinoline or 2,3-dimethylpyridine is oxidized with ozone or by a method in which 8-hydroxyquinoline is oxidized with a hypochlorite or nitric acid. However, these methods have problems, such as that the costs of the raw material or equipment are high, the yield is low, and/or waste liquor, which requires cumbersome treatment, is discharged in a large amount.

The present invention provides a process for producing 2,3-pyridine-dicarboxylic acid in which the above-described problems are alleviated so that the process is suitable for application to commercial production.

As is known to those skilled in the art, mother liquor remaining after precipitated 2,3-pyridinedicarboxylic acid has been separated out still contains a considerable amount of 2,3-pyridinedicarboxylic acid, but this mother liquor has not been utilized in an effective manner. This is one of the causes for the low yields in the prior art methods. In addition, the entire mother liquor is treated as waste liquor, thus requiring increased costs for treatment of waste liquor.

If the mother liquor is recirculated to the step of preparing 2,3-pyridine-dicarboxylic acid, the 2,3-pyridinedicarboxylic acid contained in the mother liquor can be effectively utilized while the costs of waste liquor treatment can be restrained. However, the mother liquor also contains, in addition to 2,3-pyridinedicarboxylic acid, significant amounts of organic by-products formed during the synthesis of 2,3-pyridinedicarboxylic acid. Therefore, use of the recirculated mother liquor in the preparation step leads to a significant decrease in the purity of the desired product, 2,3-pyridinedicarboxylic acid. This is thought to be the main reason why the mother liquor has not been positively utilized.

For example, in a typical process for producing 2,3-pyridinedicarboxylic acid via copper (II) 2,3-pyridinedicarboxylate, the copper (II) salt is decomposed by reacting with an alkali in solution to give a solution of an alkali metal salt of 2,3-pyridinedicarboxylic acid, which is then reacted with a mineral acid to precipitate 2,3-pyridinedicarboxylic acid. The precipitates are recovered as the 2,3-pyridine-dicarboxylic acid product.

With respect to the production of 2,3-pyridinedicarboxylic acid copper (II) salt by oxidizing quinoline with hydrogen peroxide in the presence of copper (II) sulfate, it is described in JP-B 60-54305 that the filtrate remaining after the copper (II) salt is recovered is recirculated to the step of preparing the copper (II) salt by the above-described oxidation of quinoline. However, the filtrate contains significant amounts of by-products, and use of the recirculated filtrate significantly deteriorates the purity of the product.

In JP-A 61-212563 which discloses a method for preparing 2,3-pyridinedicarboxylic acid by oxidizing quinoline with a hypochlorite and a ruthenium oxide catalyst in the presence of a large amount of sodium hydroxide, it is described that after sodium chloride is filtered off from the reaction mixture, an acid is added to the filtrate to precipitate 2,3-pyridinedicarboxylic acid and recover it, and 2,3-pyridinedicarboxylic acid remaining in the mother liquor, from which the precipitated product has been separated, can be recovered as its copper (II) salt by adding copper (II) oxide to the mother liquor. However, in this process, the 2,3-pyridinedicarboxylic acid copper (II) salt recovered from the mother liquor is contaminated with a large proportion of impurities since the mother liquor contains organic impurities in an overwhelmingly larger amount than 2,3-pyridinedicarboxylic acid. Therefore, the recovered copper (II) salt produces 2,3-pyridinedicarboxylic acid with low purity.

DISCLOSURE OF THE INVENTION

The present inventors noted that copper (II) ions can selectively form an insoluble salt with 2,3-pyridinedicarboxylic acid compared to by-products which can be present in a reaction mixture formed by oxidation of quinoline or its derivative. Thus, 2,3-pyridinedicarboxylic acid copper (II) salt separated as precipitates from a reaction mixture formed by oxidation in the presence of copper (II) ions is relatively pure, and when this copper (II) salt is decomposed to form an alkali metal salt by reacting with an alkali in solution, the resulting solution of an alkali metal salt of 2,3-pyridinedicarboxylic acid is almost free from organic impurities. Upon investigation, they found the following:

(1) When 2,3-pyridinedicarboxylic acid is recovered from the alkali metal salt solution by adding a mineral acid to the solution and separating the precipitates therefrom, the remaining mother liquor can be recirculated to a preceding step in the process without adversely affecting the product purity, since it is not significantly contaminated with organic impurities and still contains a considerable amount of 2,3-pyridinedicarboxylic acid, thereby making it possible to effectively utilize the 2,3-pyridinedicarboxylic acid remaining in the mother liquor and increase the yield.

(2) In particular, when the mother liquor is recirculated to a step for preparing copper (II) 2,3-pyridinedicarboxylate by oxidation of quinoline with a chlorate under acidic conditions in the presence of copper (II) ions, the oxidation reaction is accelerated so that it is completed in a significantly reduced reaction time.

(3) The mother liquor can also be effectively utilized by adding a copper (II) compound thereto to precipitate copper (II) 2,3-pyridinedicarboxylate and recover it. The recovered copper (II) salt is also highly pure, and it is useful as a raw material for preparing 2,3-pyridinedicarboxylic acid.

Thus, the present invention provides a process for producing 2,3-pyridine-dicarboxylic acid comprising (a) oxidizing quinoline or 8-hydroxyquinoline in a solvent in the presence of copper (II) ions to precipitate the copper (II) salt of 2,3-pyridinedicarboxylic acid and then separate the precipitates, (b) reacting the separated copper (II) salt with an alkali in a solvent to obtain a solution of an alkali metal salt of 2,3-pyridinedicarboxylic acid, and (c) reacting the solution of the alkali metal salt with a mineral acid to precipitate 2,3-pyridinedicarboxylic acid and then separate the precipitates.

The process according to the present invention is characterized in that (A) part or all of the solution obtained after the precipitated 2,3-pyridinedicarboxylic acid is separated in step (c) is used as at least part of the solvent in step (a) or (b), or (B) copper or a copper compound is added to the solution obtained after the precipitated 2,3-pyridinedicarboxylic acid is separated in step (c) to recover the 2,3-pyridinedicarboxylic acid remaining in the solution as its copper (II) salt. The recovered copper (II) salt is preferably recirculated to step (b).

The process mentioned in (A) above is similar to the method described in JP-B 60-54305 in that a solution (mother liquor) obtained after separation of a precipitated product is recirculated for use as a raw material. However, the solution that is recirculated by the method of JP-B 60-54305 is a solution obtained by separating 2,3-pyridinedicarboxylic acid copper (II) salt, which is substantially insoluble. This solution is very lean in the amount of 2,3-pyridinedicarboxylic acid which it contains, and it contains much larger amounts of organic impurities. In contrast, the solution that is recirculated according to the present invention is a solution obtained by decomposing the copper (II) salt to form a solution of an alkali metal salt, then precipitating 2,3-pyridinedicarboxylic acid by acidifying the solution, and separating the precipitates, and it contains a considerable amount of 2,3-pyridinedicarboxylic acid and has a very low content of organic impurities. Therefore, unlike the method of JP-B 60-54305, the use of a recirculated solution does not cause accumulation of impurities in the reaction system and can avoid the problem that the purity of the 2,3-pyridinedicarboxylic acid product is decreased due to the accumulated impurities.

On the other hand, the process mentioned in (B) above is similar to the method described in JP-A 61-212563 in that copper or a copper compound is added to a solution from which the product has been separated and which still contains 2,3-pyridinedicarboxylic acid, thus recovering 2,3-pyridinedicarboxylic acid remaining in the solution as its copper (II) salt. However, in the method of JP-A 61-212563, the solution that is treated is obtained by separating 2,3-pyridinedicarboxylic acid which has been precipitated directly from a reaction mixture to form the product by oxidation and which contains organic impurities in a considerable amount. Therefore, the copper (II) salt which is recovered from the solution is of low purity, and recirculation of the recovered copper (II) salt in the reaction system contaminates the system. In contrast, the solution that is treated in the process according to the present invention is obtained from 2,3-pyridinedicarboxylic acid copper (II) salt by subjecting it to alkali decomposition and then acidification, and most of the organic impurities formed by the oxidation reaction to form 2,3-pyridinedicarboxylic acid have been removed. Therefore, the copper (II) salt recovered from the solution has a high purity, and recirculation of the recovered copper (II) salt can prevent contamination of the reaction system.

Preferably, the oxidation in step (a) is carried out by oxidizing quinoline or 8-hydroxyquinoline with a chlorate as an oxidizing agent under acidic conditions.

The solution of an alkali metal salt of 2,3-pyridinedicarboxylic acid obtained in step (b) may be purified, prior to treatment in step (c), by adding at least one substance selected from sulfides, hydrosulfides, polysulfides, and sulfur and removing the resulting precipitates. The solvent is preferably water in each reaction.

DESCRIPTION OF EMBODIMENTS OF THE INVENTION

Step (a):

In step (a), copper (11) 2,3-pyridinedicarboxylate is formed by oxidation of quinoline or 8-hydroxyquinoline in a solvent in the presence of copper (II) ions. The oxidation product, copper (II) 2,3-pyridinedicarboxylate, is insoluble, so it is precipitated from the resulting reaction mixture. The solvent is preferably water, but a mixed solvent of water and a water-miscible organic solvent can be used. The present invention will be described below with respect to an embodiment in which the solvent is water and the raw material is quinoline.

The formation of copper (II) 2,3-pyridinedicarboxylate by oxidation of quinoline in the presence of copper (II) ions can be performed using hydrogen peroxide as an oxidizing agent as described in JP-B 60-54305 and Chem. Ber. 65, 11

(1932). However, it is preferable from the standpoint of commercial production to follow the method described in JP-A 62-209063, i.e., to oxidize quinoline with a chlorate in an aqueous medium under acidic conditions in the presence of copper (II) ions.

The oxidation reaction can be carried out by charging a suitable reactor with the raw material (quinoline) along with water as a solvent, a mineral acid, a chlorate as an oxidizing agent, and a source of copper (II) ions. The source of copper (II) ions may be a copper (II) compound, or the copper (II) ions may be formed in situ from copper metal or a copper (I) compound by the action of the oxidizing agent.

Mineral acids which are useful includes sulfuric acid, nitric acid, and hydrochloric acid. The chlorate is preferably an alkali metal chlorate. The source of copper (II) ions is preferably a copper (II) salt, such as copper (II) sulfate, or copper (II) oxide. It is preferable in view of the yield that the chlorate be used in an amount of at least about 3.0 moles and that copper (II) ions be present in an amount of from about 0.5 moles to 2.0 moles for each mole of quinoline. The reaction temperature is typically at or nearly the reflux temperature. Since the oxidation reaction is exothermic, the reaction mixture may be cooled as required after the temperature reaches the desired reaction temperature. The reaction time is usually between about 15 and 20 hours.

As the oxidation reaction proceeds, copper (II) 2,3-pyridinedicarboxylate is precipitated out of the reaction mixture which was initially an aqueous solution. At the end of the oxidation reaction, the reaction mixture is filtered to separate the precipitated copper (II) 2,3-pyridinedicarboxylate. Thus, a wet cake of copper (II) 2,3-pyridinedicarboxylate is obtained.

As described previously, copper (II) ions form an insoluble salt selectively with 2,3-pyridinedicarboxylic acid to form precipitates, and various organic impurities which are formed as by-products during the oxidation reaction remain in solution. Therefore, the cake of copper (II) 2,3-pyridinedicarboxylate which has been separated from the solution after the oxidation reaction is of relatively high purity, and its content of organic impurities is very low. On the other hand, the filtrate remaining after the copper (II) salt has been separated contains various organic impurities along with copper (II) 2,3-pyridinedicarboxylate. It is described in JP-B 60-54305 that this filtrate remaining after separation of the copper (II) salt is recirculated to the oxidation reaction of quinoline. However, if the filtrate is so used, impurities are accumulated in the oxidation reaction system, thereby adversely affecting the purity of the product. Therefore, in the process according to the present invention, the solution (filtrate) obtained after separation of the copper (II) salt is discarded. Since the solubility of the copper (II) salt is extremely low compared to that of free 2,3-pyridinedicarboxylic acid, the filtrate has a low content of 2,3-pyridinedicarboxylic acid, and discarding of the filtrate does not adversely affect the yield to a great extent.

Step (b):

The cake of copper (II) 2,3-pyridinedicarboxylate obtained in step (a) is reacted with an alkali in water as a solvent, thereby decomposing the copper (II) salt into an alkali metal salt to give an aqueous solution of an alkali metal 2,3-pyridine-dicarboxylate.

This alkali decomposition step can be performed by mixing the cake of the copper (II) salt with an aqueous solution of an alkali, which is usually sodium hydroxide or potassium hydroxide. The alkali decomposition is generally carried out at a temperature which ranges from room temperature to the reflux temperature. The alkali is preferably used in an excess amount, i.e., in an amount larger than the stoichiometric amount required for the decomposition of the copper (II) salt.

The alkali decomposition gives an alkali metal salt of 2,3-pyridinedicarboxylic acid, which is dissolved in the reaction mixture, and precipitates of copper (II) oxide as a by-product. The precipitates of copper (II) oxide are removed from the reaction mixture by a suitable means such as filtration so that an aqueous solution of an alkali metal 2,3-pyridinedicarboxylate is obtained as the product of step (b).

As described above, the copper (II) salt of 2,3-pyridinedicarboxylic acid which is the raw material in step (b) is of relatively high purity, so the copper (II) oxide removed by filtration is also of relatively high purity. Therefore, the copper (II) oxide removed in step (b) can be recirculated to step (a) as a source of copper (II) ions without purification. Thus, the source of copper (II) ions which is initially supplied to the reaction in step (a) can be used repeatedly in step (a) while a small amount thereof is supplemented to compensate for losses caused by filtration or the like.

Step (c):

The aqueous solution of an alkali metal 2,3-pyridinedicarboxylate obtained in step (b) is acidified with a mineral acid to precipitate 2,3-pyridinedicarboxylic acid, which is then separated. Thus, the reaction in step (c) is an acidification reaction to precipitate 2,3-pyridinedicarboxylic acid, which is the desired product of the process according to the present invention and is recovered as a wet cake. The wet cake can be dried to obtain a powder product of 2,3-pyridinedicarboxylic acid. The mineral acid may be a usual one such as hydrochloric acid, sulfuric acid, or nitric acid.

If desired, the aqueous solution of an alkali metal 2,3-pyridinedicarboxylate which is subjected to acidification may be purified. The purification can be performed by any suitable method. A preferable method for purifying the aqueous solution is performed by adding at least one substance selected from sulfides, hydrosulfides, polysulfides, and sulfur to the solution so as to cause heavy metal ions (mainly comprising copper (II) ions) present in the solution to precipitate as their sulfides and removing the resulting precipitates by filtration or other method. If the aqueous solution which is used in the reaction in step (c) is purified in this manner, the 2,3-pyridinedicarboxylic acid product obtained in step (c) becomes highly pure, and it has significantly decreased content of heavy metals. Thus, it is possible to obtain 2,3-pyridinedicarboxylic acid having a heavy metal content of less than 25 mg/kg and preferably 5 mg/kg or less as determined in accordance with the heavy metal assay, the second method specified in the Japanese Pharmacopeia, or a copper content of less than 20 mg/kg and preferably 5 mg/kg or less determined by ICP analysis of a solution of an ashed sample dissolved in a mineral acid. In addition to copper, the content of iron, which tends to dissolve out from the equipment used in the commercial-scale production of a product and contaminate the product, can be decreased to the same level as copper.

The solution (mother liquor) remaining after 2,3-pyridinedicarboxylic acid has been separated contains 2,3-pyridinedicarboxylic acid in an amount of 1–5% depending on the temperature and pH. As a result, approximately 5–25% of 2,3-pyridinedicarboxylic acid which was formed by acidification does not precipitate and remains in the mother liquor, although the proportion of the remaining acid varies with the amount of the mother liquor. Since the copper (II) salt product formed in step (a) is of relatively high purity, the mother liquor obtained in step (c) also has a decreased content of organic impurities, and recirculation of this mother liquor causes little contamination of the reaction system.

Therefore, in the process according to the present invention, the mother liquor obtained in step (c) is recirculated to step (a) and/or step (b) for use as at least part of the solvent (water) used in the step. As a result, the 2,3-pyridinedicarboxylic acid present in the mother liquor can be effectively used without a significant adverse effect on the product quality, thereby increasing the yield and decreasing the amount of waste liquor which must be treated. Since the mother liquor obtained in step (c) is strongly acidic, the mother liquor may be neutralized at least partially with an alkali, if necessary, prior to recirculation, particularly to step (b).

There is substantially no problem when the mother liquor obtained in step (c) is recirculated to the oxidation step (a). In this case, when the oxidation in step (a) is carried out under acidic conditions, such recirculation is also advantageous in that the amount of the acid which is supplied to step (a) can be significantly reduced. In the case where the mother liquor is recirculated to the alkali decomposition step (b), some impurities, particularly inorganic salts, may accumulate in the reaction, thereby adversely affecting the quality of the 2,3-pyridinedicarboxylic acid product obtained in step (c). In such a case, it is preferred to purify the aqueous solution of an alkali metal 2,3-pyridinedicarboxylate obtained in step (b) by the above-described method, or to stop the recirculation of the mother liquor to step (b) and renew the solvent (water) in step (b), while the product quality is monitored by suitable analysis. When the mother liquor is recirculated to the oxidation step (a), it is of course possible to purify the aqueous solution obtained in step (b) before it is subjected to the acidification in step (c), thereby further suppressing accumulation of impurities in the reaction system.

Surprisingly, it has been found that when the oxidation of quinoline in step (a) is carried out using a chlorate as an oxidizing agent under acidic conditions in the presence of copper (II) ions, recirculation of the mother liquor to step (a) can accelerate the oxidation reaction significantly so that the reaction time required to complete the oxidation is greatly reduced. For example, the reaction time, which is 17 hours without such recirculation, is reduced to 10 hours. Thus, the production costs can be significantly reduced according to the present invention, also due to this reduced reaction time, in addition to the increased yield and decreased amount of waste liquor.

The 2,3-pyridinedicarboxylic acid present in the mother liquor obtained in step (c) may be recovered as its copper (II) salt, instead of the mother liquor being recirculated to step (a) and/or step (b). As described above, since copper (II) 2,3-pyridinedicarboxylate is substantially insoluble, almost all the 2,3-pyridine-dicarboxylic acid present in the mother liquor can be recovered by precipitating it in the form of its copper (II) salt.

The precipitation of the copper (II) salt can be performed by adding to the mother liquor a copper (II) compound alone, or copper metal or a copper (II) compound along with an oxidizing agent such as nitric acid, a hypochlorite, or chlorate. The amount of copper which is added is preferably in excess relative to the 2,3-pyridinedicarboxylic acid present in the mother liquor (e.g., about twice or more the stoichiometric amount). The precipitated copper (II) salt is recovered by filtration or other method.

It is preferred in view of maintaining the product quality that the recovered copper (II) salt be recirculated to step (b) for use as part of the raw material which is subjected to alkali decomposition in this step.

Recovery of 2,3-pyridinedicarboxylic acid as its copper (II) salt from a mother liquor obtained by separation of 2,3-pyridinedicarboxylic acid is also described in JP-A 61-212563. However, in the method described therein, the mother liquor contains a considerable amount of impurities since it is obtained from the reaction mixture of an oxidation reaction without the formation of a copper (II) salt. Therefore, the copper (II) salt recovered from such mother liquor is of low purity. In the process according to the present invention, the mother liquor is of high purity with its content of organic impurities being low since it is obtained from the copper (II) salt by alkali decomposition and subsequent acidification. Therefore, the copper (II) salt recovered from the mother liquor obtained in step (c) is relatively pure, and recirculation of this salt to step (a) has little adverse effect on the purity of the product.

From a commercial standpoint, recirculation of the mother liquor obtained in step (c) to step (a) and/or (b) is more advantageous than recovery of the copper (II) salt from the mother liquor since the latter requires extra steps for precipitating the copper (II) salt and recovering it.

By recirculating the mother liquor obtained in step (c) to step (a) and/or step (b) or recirculating the copper (II) salt recovered from this mother liquor to step (b), it is possible to increase the yield by approximately 7–15%. An increase in yield to such a level is of great significance in the commercial production of 2,3-pyridine-dicarboxylic acid.

In addition, particularly when the solution of an alkali metal salt of 2,3-pyridinedicarboxylic acid obtained by the alkali decomposition step (b) is purified with a sulfide or similar substance, it is possible to obtain a product having a decreased content of heavy metals such as copper. In the field of drugs, the copper content of a product is frequently limited to less than 25 mg/kg. In the process according to the present invention, in spite of recirculation of a mother liquor, it is possible to produce 2,3-pyridinedicarboxylic acid having a copper content of less than 25 mg/kg.

Needless to say, the process according to the present invention can be performed by continuous, semi-continuous, or batch modes.

In the process for producing 2,3-pyridinedicarboxylic acid according to the present invention, part of the waste liquor which has been discarded can be effectively used by recirculating it to the process without adversely affecting the purity of the product, thereby making it possible to produce highly pure 2,3-pyridinedicarboxylic acid with an increased yield and with decreased costs for treating the waste liquor. In an embodiment of the present invention, it is also possible to significantly reduce the time required for oxidation of quinoline into copper (II) 2,3-pyridinedicarboxylate. Thus, the present invention is suitable for application to commercial production of 2,3-pyridinedicarboxylic acid, for which there was no established process in the past.

EXAMPLES

In the following examples including a comparative and a reference example, all the percentages (except for percentage of yield which is a mole percent) are by weight unless otherwise indicated.

Comparative Example 1

Referring to an example described in JP-A 62-209063, 2,3-pyridine-dicarboxylic acid was prepared starting from quinoline in the following manner.

A glass flask was charged with 34.8 grams of quinoline, 270 grams of water, 67.4 grams of copper (II) sulfate pentahydrate, 33.8 grams of 98% sulfuric acid, and 101.2 grams of sodium chlorate and heated at 98–103° C. for 17 hours to perform oxidation of quinoline. The resulting precipitates of 2,3-pyridinedicarboxylic acid copper (II) salt were separated by filtration.

The separated wet cake of the copper (II) salt was mixed with a solution of 25 grams of sodium hydroxide dissolved in 150 grams of water, and the mixture was is heated at 70° C. for 1 hour to subject the copper (II) salt to alkali decomposition. The copper (II) oxide which had been precipitated as a by-product was then removed by filtration with washing with water, and 285 grams of an aqueous solution of 2,3-pyridinedicarboxylic acid sodium salt were obtained as a filtrate.

The aqueous solution of the sodium salt was acidified to a pH of 1 with 35% hydrochloric acid to precipitate 2,3-pyridinedicarboxylic acid by acidification. The resulting precipitates were collected by filtration and dried to give 22.9 grams of 2,3-pyridinedicarboxylic acid. The purity of the product was 99.8% and the yield was 50.9%. The volume of the filtrate was 350 grams including the washings, and it contained 1.3% of 2,3-pyridinedicarboxylic acid. Thus, the amount of 2,3-pyridinedicarboxylic acid present in the filtrate was 4.6 grams.

Example 1

The oxidation, alkali decomposition, and acidification reactions were carried out in the same manner as described in Comparative Example 1 except that a 270 gram aliquot of the 350 gram filtrate obtained in that example after the 2,3-pyridinedicarboxylic acid product had been separated in the acidification step was used in place of water in the oxidation step. The progress of the oxidation reaction was monitored by periodical analysis of the reaction mixture, indicating that the oxidation reaction completed after 10 hours, so the reaction time of the oxidation reaction was reduced to 10 hours.

In the acidification step, 26.2 grams of 2,3-pyridinedicarboxylic acid having a purity of 99.9% was obtained with a yield of 58.2%. The volume of the filtrate remaining after separation of this product was 350 grams including the washings, and it contained 1.3% of 2,3-pyridinedicarboxylic acid. Thus, the amount of 2,3-pyridine-dicarboxylic acid present in the filtrate was 4.6 grams.

Example 2

The oxidation, alkali decomposition, and acidification reactions were carried out in the same manner as described in Comparative Example 1 except that a 150 gram aliquot of the 350 gram filtrate obtained in Example 1 in the acidification step is was used as the water to dissolve sodium hydroxide in the alkali decomposition step.

In the acidification step, 24.6 grams of 2,3-pyridinedicarboxylic acid having a purity of 99.9% was obtained with a yield of 54.6%. The volume of the filtrate remaining after separation of this product was 350 grams including the washings, and it contained 1.3% of 2,3-pyridinedicarboxylic acid. Thus, the amount of 2,3-pyridine-dicarboxylic acid present in the filtrate was 4.6 grams.

Example 3

The oxidation, alkali decomposition, and acidification reactions were carried out in the same manner as described in Comparative Example 1 except that a 270 gram aliquot of the 350 gram filtrate obtained in Example 2 in the acidification step was used in place of water in the oxidation step and the remaining 80 gram aliquot of the filtrate was used as the water to dissolve sodium hydroxide in the alkali decomposition step. As in Example 1, the reaction time of the oxidation reaction was reduced to 10 hours.

In the acidification step, 27.7 grams of 2,3-pyridinedicarboxylic acid having a purity of 99.9% were obtained with a yield of 61.5%. The volume of the filtrate remaining after separation of this product was 350 grams including the washings, and it contained 1.3% of 2,3-pyridinedicarboxylic acid. Thus, the amount of 2,3-pyridinedicarboxylic acid present in the filtrate was 4.6 grams.

Example 4

To the 350 gram filtrate obtained in Example 3 after the 2,3-pyridine-dicarboxylic acid product had been separated in the acidification step, 10.5 grams of copper (II) sulfate pentahydrate, which were equal to 2 moles per mole of 2,3-pyridinedicarboxylic acid present in the filtrate, were added, and the solution was stirred. The resulting precipitates of copper (II) 2,3-pyridinedicarboxylate were recovered by filtration, and the recovered copper (II) salt was then subjected to alkali decomposition and acidification in the same manner as described in Comparative Example 1. In this manner, 3.6 grams more of 2,3-pyridinedicarboxylic acid product having a purity of 99.9% were obtained.

Instead of subjecting the recovered copper (II) salt of 2,3-pyridinedicarboxylic acid to alkali decomposition and acidification independently as illustrated in this example, the recovered copper (II) salt may be recirculated to the alkali decomposition step.

In either case, it is possible to increase the yield by about 8% compared to Comparative Example 1.

Reference Example 1

The oxidation, alkali decomposition, and acidification reactions were carried out in the same manner as described in Comparative Example 1 except that the solution of the sodium salt obtained after the alkali decomposition was purified before it was reacted with a mineral acid for acidification. The purification was performed by adding 0.3 grams of sodium sulfide to the solution, stirring the solution for 30 minutes at 70° C., and removing the resulting precipitates by filtration.

The content of heavy metal impurities of the purified solution (aqueous solution of 2,3-pyridinedicarboxylic acid sodium salt) was determined by the ashing-ICP method in which a sample solution was ashed and the resulting ash was dissolved in a mineral acid (hydrochloric acid) and subjected to ICP analysis. The limit of detection in this ashing-ICP method was 1 mg/kg. Thus, a content which is expressed as "<1 mg/kg" indicates that the content was lower then the limit of detection. The results are shown in the following table along with the results for the same solution before purification.

TABLE 1

Heavy metal content of aqueous solution of sodium salt (mg/kg)

|  | Iron | Copper |
|---|---|---|
| Before purification | 13 | 130 |
| After purification | <1 | <1 |

It can be seen from the above table that purification of the aqueous solution obtained in the alkali decomposition step of copper (II) 2,3-pyridinedicarboxylate can significantly decrease the heavy metal content of the solution. Therefore, it is possible to obtain highly pure 2,3-pyridinedicarboxylic acid having a significantly decreased impurity content by subjecting the purified solution to the acidification step.

In the present invention, recirculation of the mother liquor obtained in the acidification step arouses the concern that heavy metal impurities such as copper might accumulate in the reaction system. Even in the case where the mother liquor is recirculated to the alkali decomposition step, if the solution obtained in the alkali decomposition step is purified in the above-described manner by addition of a sulfide or similar substance as required, it is possible to obtain 2,3-pyridinedicarboxylic acid having a significantly decreased heavy metal content.

What is claimed is:

1. A process for producing 2,3-pyridinedicarboxylic acid comprising (a) oxidizing quinoline or 8-hydroxyquinoline in a solvent in the presence of copper (II) ions to precipitate copper (II) salt of 2,3-pyridinedicarboxylic acid and then separating the precipitates, (b) reacting the separated copper (II) salt with an alkali in a solvent to obtain a solution of an alkali metal salt of 2,3-pyridinedicarboxylic acid, and (c) reacting the solution of the alkali metal salt with a mineral acid to precipitate 2,3-pyridinedicarboxylic acid and then separating the precipitates, wherein part or all of the solution obtained after the precipitated 2,3-pyridinedicarboxylic acid is separated in step (c) is used as at least part of the solvent in step (a) or (b).

2. The process of claim 1, wherein the oxidation in step (a) is carried out by oxidizing quinoline or 8-hydroxyquinoline with a chlorate as an oxidizing agent under acidic conditions.

3. The process of claim 1, wherein the solution of an alkali metal salt of 2,3-pyridinedicarboxylic acid obtained in step (b) is purified, prior to treatment in step (c), by adding at least one substance selected from sulfides, hydrosulfides, polysulfides, and sulfur and removing the resulting precipitates.

4. The process of claim 1, wherein the solvent is water in each reaction of steps (a) and (b).

5. The process of claim 1, wherein part or all of the solution obtained after the precipitated 2,3-pyridinedicarboxylic acid is separated in step (c) is used as at least part of the solvent in step (a).

* * * * *

UNITED STATES PATENT AND TRADEMARK OFFICE
CERTIFICATE OF CORRECTION

PATENT NO.        : 6,900,330 B1                                    Page 1 of 1
APPLICATION NO. : 10/657732
DATED             : May 31, 2005
INVENTOR(S)       : Sato et al.

It is certified that error appears in the above-identified patent and that said Letters Patent is hereby corrected as shown below:

Face of the patent, See Item (73) Assignee, the first named Assignee should be: Sumikin Air Water Chemical, Inc., Tokyo, (JP), followed by the currently named Assignee: Hebei Sinochem Fuheng Co., Ltd., Hebei (CN).

Face of the patent, See, (56) References Cited, under OTHER PUBLICATIONS, the last reference is a duplicate of the first publication. Please delete the last reference to C. O'Murchu.

Column 1, line 5, "TECHNICAL FIELD" should read -- Field of the Invention --

Column 1, line 16, "BACKGROUND ART" should read -- Description of the Related Art --

Column 3, line 1, "DISCLOSURE OF THE INVENTION" should read -- Summary of the Invention --

Column 4, lines 51-52, "DESCRIPTION OF EMBODIMENTS OF THE INVENTION" should read -- Detailed Description of the Invention --

Signed and Sealed this

Fifth Day of December, 2006

JON W. DUDAS
*Director of the United States Patent and Trademark Office*